(12) United States Patent
Kim et al.

(10) Patent No.: US 11,542,468 B2
(45) Date of Patent: Jan. 3, 2023

(54) *AGATHOBACULUM* SP. STRAIN HAVING PROPHYLACTIC OR THERAPEUTIC EFFECTS ON DEGENERATIVE BRAIN DISEASES AND USE THEREOF

(71) Applicant: HEALTHBIOME, Daejeon (KR)

(72) Inventors: Byoung-Chan Kim, Daejeon (KR); Chul-Ho Lee, Daejeon (KR); Kyoung-Shim Kim, Daejeon (KR); Myung-Hee Kim, Daejeon (KR); Sang Jun Lee, Daejeon (KR); Dong-Ho Chang, Daejeon (KR); Doo-Sang Park, Daejeon (KR); Jung Hwan Hwang, Daejeon (KR); Yong-Hoon Kim, Daejeon (KR); Dong-Hee Choi, Daejeon (KR); Jung-Ran Noh, Daejeon (KR); In-Bok Lee, Daejeon (KR); Young-Keun Choi, Daejeon (KR); Yun-Jung Seo, Daejeon (KR); Jung-Hyeon Choi, Daejeon (KR); Jun Go, Daejeon (KR); Hye-Yeon Park, Daejeon (KR); Young-Kyoung Ryu, Daejeon (KR); Moon-Soo Rhee, Daejeon (KR)

(73) Assignee: HEALTHBIOME, Daejeon (KR)

( * ) Notice: Subject to any disclaimer, the term of this patent is extended or adjusted under 35 U.S.C. 154(b) by 0 days.

(21) Appl. No.: 16/303,025

(22) PCT Filed: Jun. 14, 2017

(86) PCT No.: PCT/KR2017/006173
§ 371 (c)(1),
(2) Date: Nov. 19, 2018

(87) PCT Pub. No.: WO2017/217753
PCT Pub. Date: Dec. 21, 2017

(65) Prior Publication Data
US 2019/0300972 A1 Oct. 3, 2019

(30) Foreign Application Priority Data

Jun. 14, 2016 (KR) ........................ 10-2016-0073585

(51) Int. Cl.
*C12N 1/20* (2006.01)
*A23K 10/18* (2016.01)
(Continued)

(52) U.S. Cl.
CPC ............. *C12N 1/205* (2021.05); *A23K 10/10* (2016.05); *A23K 10/18* (2016.05); *A23L 33/135* (2016.08);
(Continued)

(58) Field of Classification Search
None
See application file for complete search history.

(56) References Cited

U.S. PATENT DOCUMENTS

| 8,460,648 B2 | 6/2013 | Borody | |
| 2009/0143433 A1* | 6/2009 | Hendrix | A61K 31/12 514/321 |

FOREIGN PATENT DOCUMENTS

| KR | 1020110001493 A | 1/2011 |
| KR | 101261131 B1 | 4/2013 |

(Continued)

OTHER PUBLICATIONS

Ahn et al., Int'l. J. Syst. Evol. Microbiol. 66: 3656-3661 (2016).*
(Continued)

*Primary Examiner* — Erin M. Bowers
(74) *Attorney, Agent, or Firm* — NSIP Law

(57) ABSTRACT

Provided are an *Agathobaculum* sp. strain having prophylactic or therapeutic effects on degenerative brain diseases, and use thereof. Since the intestinal microorganism *Agathobaculum butyriciproducens* SR79 strain of the present invention may have effects of inhibiting neuroinflammation
(Continued)

and effects of improving movement regulation and cognitive and memory functions in animal models with degenerative brain diseases such as Parkinson's disease and Alzheimer's disease, the strain may be effectively used in foods, medicines, or feeds for preventing or treating brain diseases including Alzheimer's disease, Parkinson's disease, mild cognitive impairment, etc., and therefore, it is very useful in the relevant industries.

8 Claims, 9 Drawing Sheets

(51) Int. Cl.
　　　A23L 33/135　　(2016.01)
　　　A61K 9/00　　　(2006.01)
　　　A61K 35/66　　 (2015.01)
　　　A23K 10/10　　 (2016.01)
　　　C12R 1/01　　　(2006.01)
(52) U.S. Cl.
　　　CPC ............ *A61K 9/0053* (2013.01); *A61K 35/66* (2013.01); *C12N 1/20* (2013.01); *C12R 2001/01* (2021.05)

(56) References Cited

FOREIGN PATENT DOCUMENTS

| | | | |
|---|---|---|---|
| KR | 101476236 B1 | 12/2014 | |
| WO | 2016086206 A1 | 6/2016 | |
| WO | WO 2016/086206 | * | 6/2016 |

OTHER PUBLICATIONS https://www.nia.nih.gov/health/how-alzheimers-disease-treated, published Oct. 2018, accessed Mar. 29, 2021.*
Extended European Search Report for Application No. 17813576.0, dated Nov. 21, 2019, 7 pages.
Ghaisas et al., "Gut microbiome in health and disease: linking the microbiome-gut-brain axis and environmental factors in the pathogenesis of systemic and neurodegenerative diseases", Pharmacol Ther., Feb. 2016, 158, 52-62, 26 pages.
GeBank, "Agathobaculum butyriciproducensstrain SR79 16S ribosomal RNA gene, partial sequence", Oct. 31, 2017, 2 pages.
Chang et al., "*Faecalibaculum rodentium* gen. nov., sp. nov., isolated from the faeces of a laboratory mouse", Springer International Publishing, Switzerland, 2015, 1 page.
Jin et al., "Anti-oxidant and anti-inflammatory activities of macelignan in murine hippocampal cell line and primary culture of rat microglial cells", Biochemical and Biophysical Research Communications, 331, 2005, pp. 1264-1269.
Lim et al., "Antioxidant and Anti-inflammatory Activities of the Methanolic Extract of Neorhodomela aculeate in Hippocampal and Microglial Cells", Biol. Pharm. Bull., vol. 29, No. 6, pp. 1212-1216, 2006.
Ahn et al., "*Agathobaculum Butyriciproducens* gen. nov. sp. nov., a strict anaerobic, butyrate-producing gut bacterium isolated from human faeces and reclassification of Eubacterium desmolans as *Agathobaculum desmolans* comb. nov.", International Journal of Systematic and Evolutionary Microbiology, 2016, 66, pp. 3656-3661.

* cited by examiner

AGATHOBACULUM SP. STRAIN HAVING PROPHYLACTIC OR THERAPEUTIC EFFECTS ON DEGENERATIVE BRAIN DISEASES AND USE THEREOF

CROSS-REFERENCE TO RELATED APPLICATION

This application is the U.S. national phase of PCT Application No. PCT/KR2017/006173 filed on Jun. 14, 2017, which claims priority to KR Patent Application No. 10-2016-0073585 filed on Jun. 14, 2016, the disclosures of which are incorporated in their entirety by reference herein.

BACKGROUND OF THE INVENTION

1. Field of the Invention

The present invention relates to an *Agathobaculum* sp. strain having prophylactic or therapeutic effects on degenerative brain diseases, and use thereof.

2. Description of the Related Art

In modern people, memory is becoming increasingly important with rapidly changing lives, and it has become a major concern for adolescents who have a lot of learning to do as well as for old people. Degenerative brain diseases are known to cause memory loss, and it was revealed that neuroinflammation is a main cause of degenerative brain diseases in the central nerve system, such as Alzheimer's disease, Parkinson's disease, or Huntington's disease (Jin D Q et al, *Biochemical and Biophysical Research Communications*, 331: 1264-1269, 2005; Lim C S et al, *Biological and Pharmaceutical Bulletin*, 29: 1212-1216, 2006).

Recently, the number of patients with degenerative brain disease such as dementia has increased rapidly due to the increase of the elderly population. Efforts have been made to establish various therapeutic strategies to improve cognitive function and learning function declined due to dementia, etc., and to develop effective therapeutic agents. Therapeutic agents for the improvement of memory, which have been developed until now, include acetylcholine precursors, receptor agonists, acetylcholine esterase inhibitors, etc. However, therapeutic agents capable of treating the underlying cause of degenerative brain disease have not yet been developed, and commonly applicable therapeutic agents may be exemplified by Pfizer's Aricept which is an acetyl cholinesterase inhibitor, Novartis's Exelon, Janssen's Reminyl, and Lundbeck's Ebixa (Memantine) as an NMDA receptor (N-methyl-D-aspartate receptor) antagonist which has been recently approved by US FDA. However, acetylcholinesterase inhibitors merely improve the declined cognitive abilities, and there is a limit that they cannot treat the underlying cause of Alzheimer's disease. It is also known that acetylcholinesterase inhibitors temporarily alleviate symptoms only in some patients, and it is difficult to expect a fundamental therapeutic effect because the efficacy is not sustained for a long period of time. In addition, since degenerative brain diseases require the long-term use of the drugs due to the nature thereof, such drugs have problems of various side-effects including hepatic toxicity, vomiting, and loss of appetite. Therefore, it is urgent to develop a new therapeutic agent capable of preventing the progression of degenerative brain diseases. To this end, many multinational pharmaceutical companies are investing heavily in research and development in this field, and particularly, they have focused on the development of beta or gamma secretase inhibitors capable of reducing production of β-amyloid consisting of about 40 amino acids, which is thought to be the underlying cause of Alzheimer's disease. In Korea, basic researches on Alzheimer's disease have been conducted to a certain extent, but it is considered that therapeutic agents for dementia have been rarely developed.

Recent studies have revealed that intestinal microorganisms actively influence the control of brain function and the onset of brain diseases as well as the intestinal health and intestinal diseases in humans. However, there have been no reports of prophylactic or therapeutic effects of a novel intestinal microorganism *Agathobaculum butyriciproducens* SR79 strain on brain diseases and its effects on cognitive and memory functions.

Meanwhile, Korean Patent No. 1476236 discloses "lactic acid bacteria capable of preventing and/or treating senescence and dementia", and Korean Patent No. 1261131 discloses "a novel tacrolimus derivative, a neuroprotective composition including the derivative, an immunosuppressive composition including the derivative, a method of preparing the derivative, and a strain producing the derivative", but there have been no reports of "an *Agathobaculum* sp. strain having a prophylactic or therapeutic effect on degenerative brain diseases, and use thereof" as in the present invention.

The present invention has been made in view of the above-described needs, and many effort have been made to develop a novel prophylactic or therapeutic agent for degenerative brain diseases by using a substance showing no toxicity to the human body even when ingested, wherein the prophylactic or therapeutic agent is a safe drug having no side effects and capable of effectively inhibiting and treating the onset and progression of degenerative brain diseases such as Parkinson's disease and Alzheimer's disease which are becoming increasingly common in the modern world. As a result, it was found that a novel intestinal microorganism *Agathobaculum butyriciproducens* SR79 strain may improve movement disorders in animal models with Parkinson's disease, may have inhibitory effects on neuroinflammation, and may have effects of suppressing expression of a marker for a degenerative brain disease such as Alzheimer's disease and effects of improving cognitive and memory functions, and thus the strain may be used in preventing or treating degenerative brain diseases and in improving cognitive and memory functions, thereby completing the present invention.

SUMMARY OF THE INVENTION

In order to solve the above objects, the present invention provides an *Agathobaculum* sp. strain having prophylactic or therapeutic effects on degenerative brain diseases.

Further, the present invention provides a pharmaceutical composition for preventing or treating degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

Further, the present invention provides a health functional food composition for preventing or improving degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

Further, the present invention provides a feed composition for preventing or improving degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

DETAILED DESCRIPTION OF THE PREFERRED EMBODIMENTS

Figure 1:
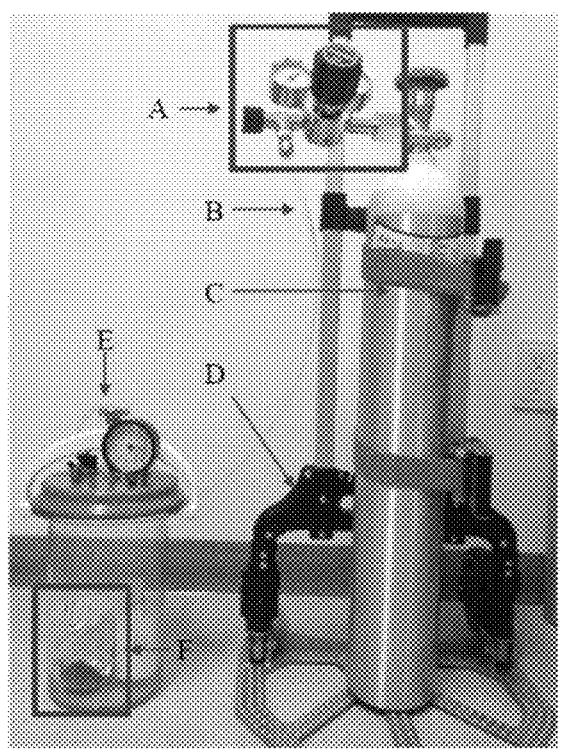
FIG. 1 shows a mobile sample collection bin used in the present invention for absolute anaerobic storage and transportation of clinical samples which were collected from stool samples of healthy Korean pregnant women (A: gas regulator, B: gas line, C: aluminum gas cylinder (gas mixture: $N_2:H_2:CO_2=86:7:7$), D: gas cylinder trolley, E: pressurized anaerobic jar (Oxoid), F: palladium (catalyst)).

In order to achieve the above objects of the present invention, the present invention provides an *Agathobaculum* sp. strain having prophylactic or therapeutic effects on degenerative brain diseases.

In the strain according to an aspect of the present invention, the *Agathobaculum* sp. strain may be *Agathobaculum butyriciproducens*, and preferably, the *Agathobaculum butyriciproducens* may be an *Agathobaculum butyriciproducens* SR79 strain with Accession No. KCTC13036BP, but is not limited thereto.

The *Agathobaculum butyriciproducens* SR79 strain according to the present invention is an absolute anaerobic microorganism isolated by the present inventors directly from the intestine of a healthy Korean, and it was confirmed by molecular biological, physiological/biochemical microbiological identification methods that the strain is a novel microorganism belonging to a novel genus and species different from the standard strain previously reported. The name of the microorganism was suggested as *Agathobaculum butyriciproducens* SR79. The SR79 strain identified in the present invention was accepted by the International Journal of Systematic and Evolutionary Microbiology as a standard strain for the genus and species of *Agathobaculum butyriciproducens*, which is the new scientific name proposed by the present inventors.

Use of the novel isolated microorganism, i.e., the *Agathobaculum butyriciproducens* SR79 strain, in the prevention or treatment of degenerative brain diseases has never been disclosed, and the present inventors demonstrated for the first time that this strain has effects of preventing or treating degenerative brain diseases including Alzheimer's disease, Parkinson's disease, etc. and effects of improving cognitive and memory functions. The previous dissertation (Pharmacology & Therapeutics 2016. 158: 52-62) reported that the intestinal microorganisms of patients with dementia such as Alzheimer's disease, Parkinson's disease, etc. are different from those of healthy persons. However, the present invention is the first of the patents or dissertations worldwide that substantially demonstrate the prophylactic or therapeutic effects of the intestinal absolute anaerobic microorganism of healthy persons on dementia such as Alzheimer's disease, Parkinson's disease, etc. This is the first time in the world that the human symbiotic microorganism may be developed as a prophylactic or therapeutic agent for dementia.

As used herein, the term "degenerative brain disease" refers to a disease that occurs in the brain, among degenerative diseases caused by aging, but not limited to, preferably a disease selected from the group consisting of Alzheimer's disease, Parkinson's disease, mild cognitive impairment, meningitis, stroke, dementia, Huntington's disease, Creutzfeldt-Jakob disease, and combinations thereof. The degenerative brain disease is known to be caused by neuronal death resulting from agglutination of proteins due to neurodegeneration with aging or genetic, environmental factors, but its accurate cause has not yet been revealed.

As used herein, the term "prevention" means all of the actions by which the occurrence of degenerative brain disease is restrained or retarded by administration of the pharmaceutical composition according to the present invention, and the term "treatment" means all of the actions by which symptoms of a subject having or suspected of having the degenerative brain disease have taken a turn for the better or been modified favorably by administration of the pharmaceutical composition.

In the present invention, the prevention or treatment of the degenerative brain disease may be achieved by the microorganism strain having effects of inhibiting phosphorylation of an amyloid precursor protein and neuroinflammation, and ethologically, having effects of improving movement regulation and cognitive and memory functions in animal models with degenerative brain diseases such as Parkinson's disease and Alzheimer's disease.

Further, the present invention provides a pharmaceutical composition for preventing or treating degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

In the pharmaceutical composition for preventing or treating degenerative brain diseases according to one embodiment of the present invention, the composition may have an effect of inhibiting movement disorders caused by dopaminergic neuronal cell death, an effect of inhibiting neuroinflammation, or an effect of improving cognitive and memory functions, but is not limited thereto.

As used herein, the term "dopamine" is a neurotransmitter that transmits signals in the brain, and known to be associated with movement and behavior.

As used herein, the term "dopaminergic neuronal cell death" means loss or denaturation of dopaminergic neuronal cells in the substantia nigra pars compacta, and it is known that Parkinson's disease animal models in which dopaminergic neuronal cell death is induced may be prepared by injecting 6-OHDA (6-hydroxyldopamine).

As used herein, the term "neuroinflammation" is a main cause of degenerative brain diseases. When inflammatory cells are excessively activated in the brain, secretion of proinflammatory cytokines is increased, and the excessive activation of neuroinflammation may cause loss of brain cells and degenerative brain diseases such as Parkinson's disease and Alzheimer's disease.

As described above, the SR79 strain provided in the present invention was confirmed to have the effect of inhibiting neuroinflammation. The SR79 strain also may improve movement regulation and cognitive and memory functions in animal models with degenerative brain diseases such as Parkinson's disease and Alzheimer's disease.

Figure 3:
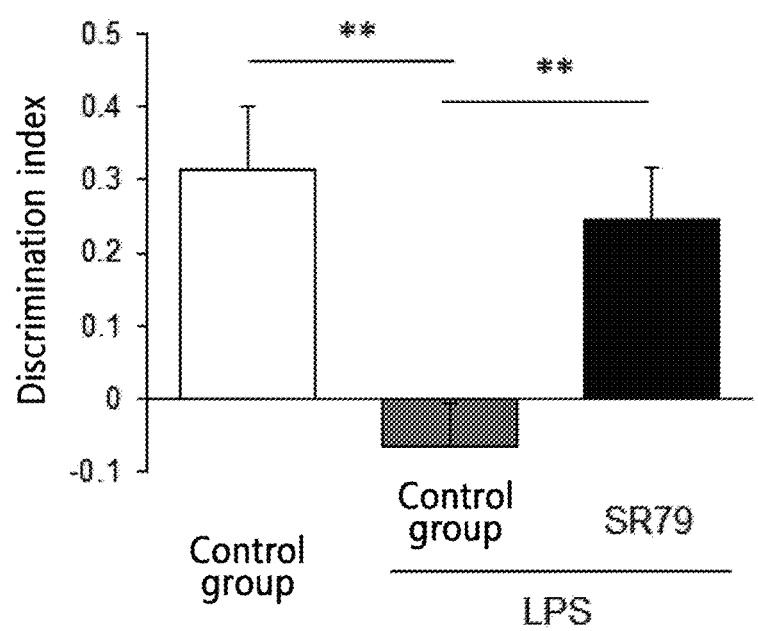
FIG. 3 is a graph showing the effects of improving cognitive and memory functions in a novel object recognition test (NORT), wherein the test was performed after administering mice, in which cognitive impairment was induced by LPS administration, with a SR79 strain which is the intestinal microorganism according to the present invention.
Figure 4:
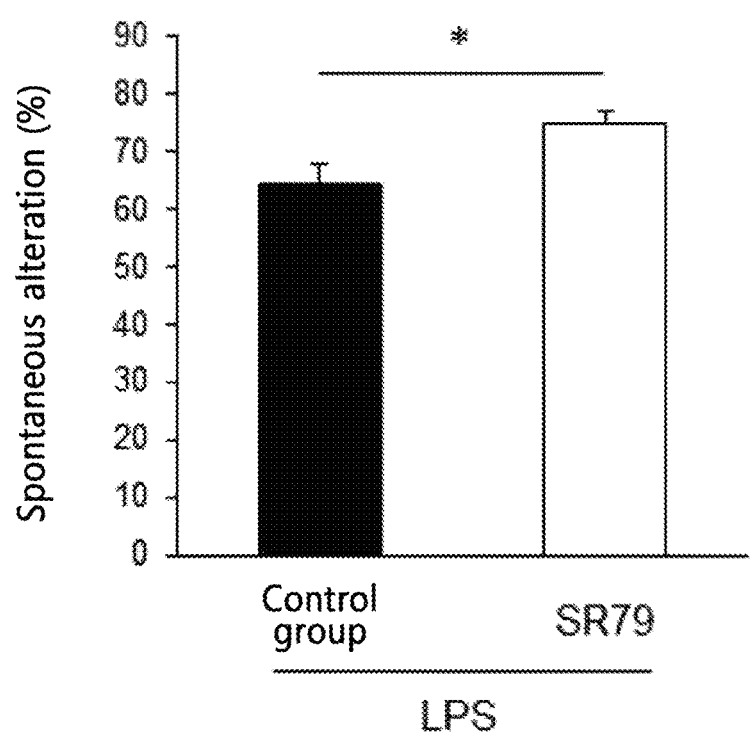
FIG. 4 is a graph showing the effects of improving spatial perception and short-term memory in a Y-maze test, wherein the test was performed after administering mice, in which cognitive impairment was induced by LPS administration, with a SR79 strain which is the intestinal microorganism according to the present invention.
Figure 6:
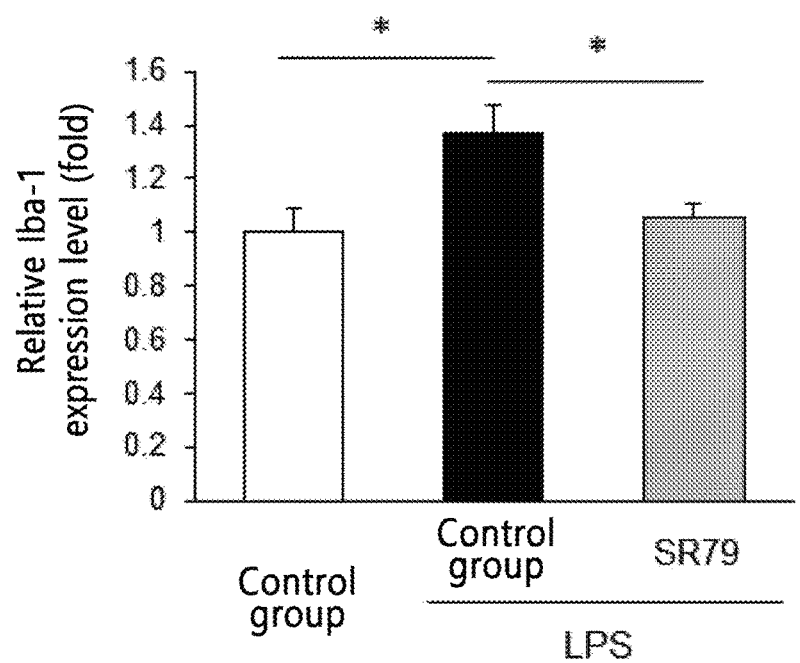
FIG. 6 is a graph showing reduced expression of Iba-1 (ionized calcium-binding adapter molecule 1) in the cerebral cortex of LPS-administered mouse models by administration of the intestinal microorganism SR79, wherein Iba-1 is a marker for activity of microglial cells mediating neuroinflammation.
Figure 7:
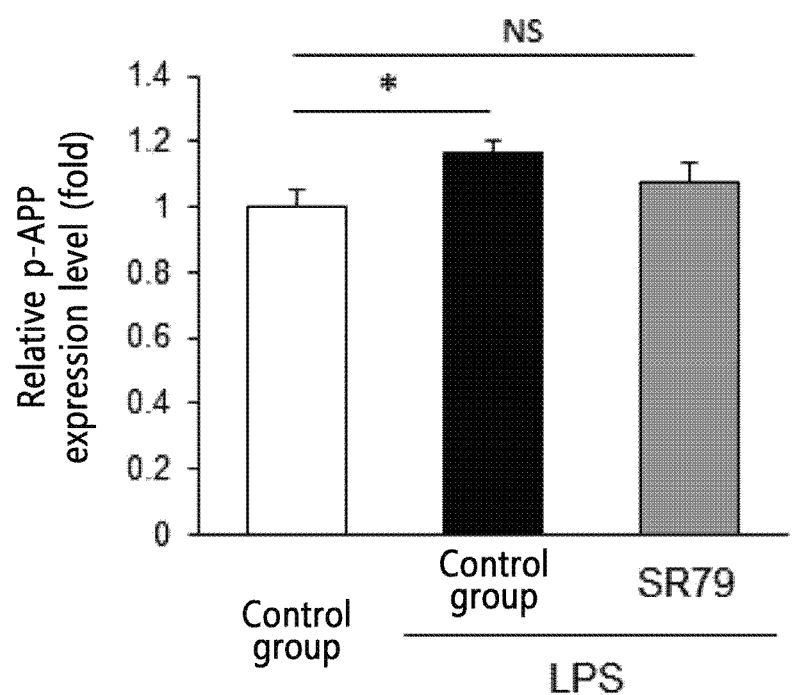
FIG. 7 is a graph showing that a remarkable increase in the expression of phosphorylated p-APP (amyloid precursor protein), which is generally increased in Alzheimer's dementia, was observed in the cerebral cortex of a mouse model administered with only LPS whereas the expression of p-APP was not increased in a group administered with both LPS and SR79 strain.
Figure 8:
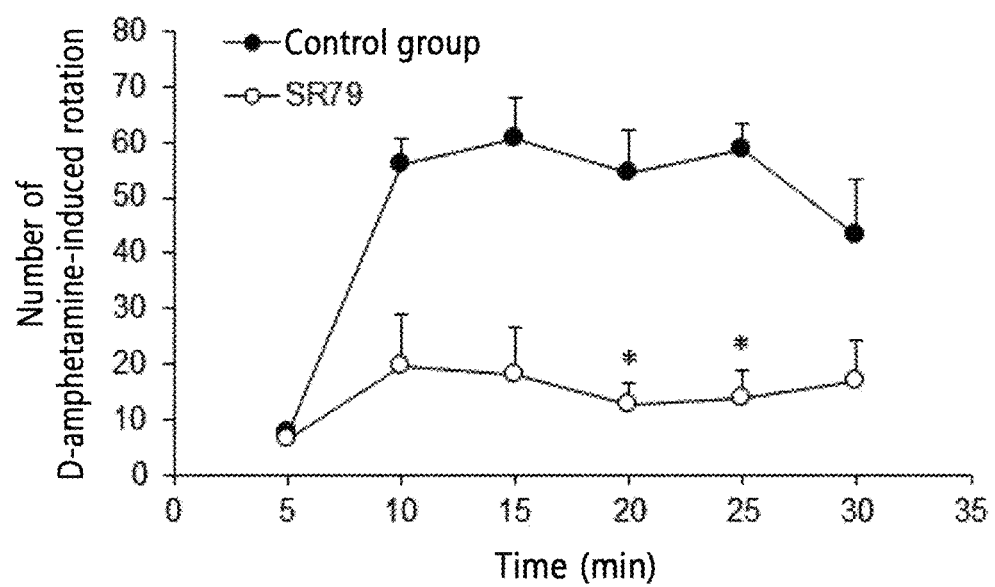
FIG. 8 is a graph showing inhibition of dextroamphetamine-induced rotational behaviors by administration of the intestinal microorganism SR79 strain, as measured every 5 minutes in a Parkinson's disease mouse animal model having 6-OHDA-induced dopaminergic neuronal cell death in the brain.
Figure 9:
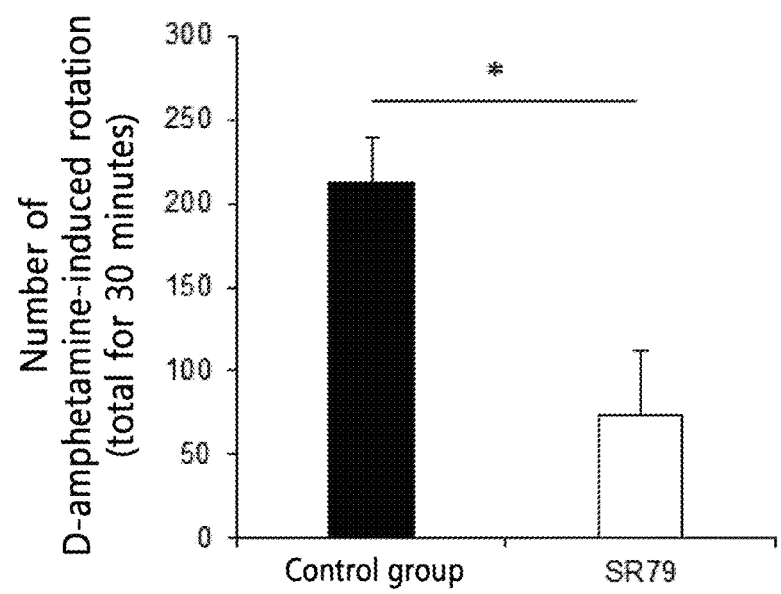
FIG. 9 is a graph showing inhibition of dextroamphetamine-induced rotational behaviors by administration of the intestinal microorganism SR79 strain, as measured for a total of 30 minutes in the Parkinson's disease mouse animal model having 6-OHDA-induced dopaminergic neuronal cell death in the brain.

According to one embodiment of the present invention, it was confirmed that administration of the microorganism strain of the present invention may improve cognitive function for a new object in mice with cognitive impairment and mouse animal models with Alzheimer's dementia (FIGS. 2 and 3) and may improve spatial perception and short-term memory abilities for Y-maze (FIG. 4). It was also confirmed that the expression of Ibal, which is a marker for microglial cells activated in the cerebral cortex, and the expression of GFAP, which is a marker for astrocyte, were remarkably reduced by SR79 administration (FIGS. 5 and 6). Furthermore, when the expression of phosphorylated amyloid precursor protein (p-APP) which is increased in Alzheimer's dementia was remarkably increased by LPS administration in the cerebral cortex of a control group, risk of developing Alzheimer's disease was increased, whereas co-administration of LPS and SR79 strain did not increase p-APP (FIG. 7). Dextroamphetamine-induced rotational behaviors were analyzed in mouse animal models with Parkinson's disease, in which dopaminergic neuronal cell death is induced by 6-OHDA, and as a result, it was confirmed that the rotational behaviors were remarkably reduced by the microorganism strain (FIGS. 8 and 9).

Accordingly, it was confirmed that the intestinal microorganism SR79 strain has the effect of inhibiting neuroinflammation and the effect of improving movement regulation and cognitive and memory functions in animal models with degenerative brain diseases such as Parkinson's disease and Alzheimer's disease.

The pharmaceutical composition of the present invention may further include an appropriate carrier, excipient, and diluent commonly used in the preparation of pharmaceutical compositions.

The pharmaceutical composition according to the present invention may be formulated according to a common method into oral dosage forms such as powders, granules, tablets, capsules, suspensions, emulsions, syrups, aerosols, etc., external dosage forms, suppository, or sterile injectable solution. The carrier, excipient, and diluent which may be included in the pharmaceutical composition according to the present invention may include various compounds or mixtures, including lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil. Upon formulation, the pharmaceutical composition may be prepared using a commonly used diluent or excipient, such as a filler, an extender, a binder, a humectant, a disintegrant, a surfactant, etc. A solid formulation for oral administration may include, for example, a tablet, a pill, a powder, a granule, a capsule, etc. Such solid formulations may be prepared by mixing the strain or the endoplasmic reticulum derived from the strain with at least one excipient, for example, starch, calcium carbonate, sucrose, lactose, gelatin, etc. In addition to the simple excipients, a lubricant, such as magnesium stearate or talc, may be used. A liquid formulation for oral administration may be a suspension, a solution for internal use, an emulsion, a syrup, etc. In addition to a commonly used simple diluent such as water and liquid paraffin, the formulation may include various excipients such as a humectant, a sweetener, an aromatic, a preservative, etc. A formulation for parenteral administration may include a sterilized aqueous solution, a non-aqueous solvent, a suspension, an emulsion, a lyophilized formulation, and a suppository. The non-aqueous solvent and the suspension may include propylene glycol, polyethylene glycol, a vegetable oil such as olive oil, an injectable ester such as ethyl oleate, etc. As a base of the suppository, witepsol, macrogol, Tween 61, cocoa butter, laurin butter, glycerogelatin, etc. may be used.

The pharmaceutical composition of the present invention may be administered in a pharmaceutically effective amount. The phrase "pharmaceutically effective amount" means a sufficient amount to prevent or treat a disease at a reasonable benefit/risk ratio applicable to any medical prevention or treatment, and an effective dose level may be determined by various factors including severity of a disease, drug activity, a patient's age, body weight, health conditions, sex, and sensitivity to drugs, administration time and route of the composition of the present invention, excretion rate, treatment period, drugs used along with or concurrently used with the composition of the present invention, and other factors well known in the medical field. The pharmaceutical composition of the present invention may be administered as an individual therapeutic agent or in combination with other therapeutic agents sequentially or simultaneously once or multiple times. It is important to administer a minimum amount that can achieve the maximum effect without adverse effects, considering all the factors described above.

The pharmaceutical composition of the present invention may be administered to a mammal including a human in a daily dose of $1.0 \times 10^9$ CFU. The administration frequency of the composition of the present invention may be administered once a day or several times in divided doses a day, but is not particularly limited thereto. The above administration dose does not limit the scope of the present invention in any aspect.

In still another aspect to achieve the above objects, the present invention provides a method of preventing or treating degenerative brain diseases, the method including the step of administering a pharmaceutically effective amount of the pharmaceutical composition to a subject having degenerative brain disease or at risk of having degenerative brain disease.

As described above, one or more selected from the group consisting of the intestinal microorganism SR79 strain provided in the present invention, endoplasmic reticulum derived from the strain, a culture of the strain, a concentrate of the culture, a dry product of the culture, and an extract of the culture may be used as an active ingredient of the pharmaceutical composition for preventing or treating degenerative brain diseases, and therefore, the composition may be used in preventing or treating degenerative brain diseases.

As used herein, the term "subject" may include without limitation all mammalian animals including mice, livestock, humans, etc. having degenerative brain disease or at risk of having degenerative brain disease.

In the method of the present invention for treating degenerative brain diseases, the pharmaceutical composition may be administered via any of the common routes, as long as a desired tissue can be reached. The pharmaceutical composition of the present invention may be, but not particularly limited to, administered orally or intrarectally, and on occasion, may be administered via other routes according to the desired purpose. However, since the intestinal SR79 strain may be denatured by gastric acid upon oral administration, the active ingredient of the composition for oral administration should be coated or formulated for protection against degradation in the stomach. In addition, the composition may be administered using a certain apparatus capable of transporting the active ingredient into a target cell.

Further, the present invention provides a health functional food composition for preventing or improving degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

The strain is the same as described above, and may be added to health functional foods for the purpose of preventing or improving degenerative brain diseases.

When the above-mentioned strain of the present invention or the culture thereof is used as the health functional food composition, the strain or the culture thereof may be added as it is or used along with other foods or food components, and may be appropriately used according to a common method. A mixing amount of the active ingredients may be appropriately determined according to the intended use (prevention, health, or treatment).

The food (or health functional food) of the present invention may further include components acceptable for use in food, which are commonly added in the preparation of foods. For example, when the food is prepared as a drink, it may further include, in addition to the strain of the present invention, one or more components of citric acid, liquid fructose, sugar, glucose, acetic acid, malic acid, and fruit juice.

The amount of the active ingredient in the food (or health functional food) of the present invention may be appropriately selected according to age, sex, body weight, conditions, and disease symptoms of a person who needs the food for preventing or improving degenerative brain disease, and preferably, the active ingredient may be used in a daily dose of about 0.01 g to about 10.0 g per an adult. By ingesting the food of the content, degenerative brain diseases may be prevented or improved.

Further, the present invention provides a method of preparing a microbial formulation for preventing or treating degenerative brain diseases, the method including the step of culturing the strain.

The method of the present invention for culturing the strain may be carried out according to a method commonly used in the art.

The microbial formulation of the present invention for preventing or treating degenerative brain diseases may be prepared using, as an active ingredient, the strain of *Agathobaculum* sp., preferably, *Agathobaculum butyriciproducens* strain, and most preferably *Agathobaculum butyriciproducens* SR79 strain with Accession No. KCTC13036BP. The microbial formulation for preventing or treating degenerative brain diseases according to the present invention may be prepared as a solution, a powder, a suspension, a dispersion, an emulsion, an oil dispersion, a paste, a dust, a propellant, or a granule, but is not limited thereto.

In still another aspect, the present invention provides a feed composition for preventing or improving degenerative brain diseases, the composition including, as an active ingredient, one or more selected from the group consisting of the strain, endoplasmic reticulum derived from the strain, a culture of the strain, a concentrate of the culture, a dry product of the culture, and an extract of the culture.

The strain is the same as described above, and may be added as the feed composition for the purpose of preventing or improving degenerative brain diseases. The feed composition may include a feed additive. The feed additive of the present invention corresponds to a supplementary feed according to Control of Livestock and Fish Feed Act.

As used herein, the term "feed" refers to any natural or artificial diet, meal, etc., or components of such meal intended or suitable to be eaten, taken in, or digested by animals. A kind of the feed is not particularly limited, and any feed generally used in the art may be used. Non-limiting examples of the feed may include plant-based feeds, such as grains, nuts, food by-products, seaweeds, fibers, drug by-products, fats and oils, starches, meals, grain by-products, etc.; and animal-based feeds such as proteins, inorganic matters, fats and oils, minerals, fats and oils, single cell proteins, zooplanktons, foods, etc. These may be used alone or in a mixture of two or more thereof.

Hereinafter, the construction and effects of the present invention will be described in more detail with reference to Examples. However, these Examples are for illustrative purposes only, and the scope of the present invention is not intended to be limited by these Examples.

Example 1: Collection of Stool Samples of Korean Healthy Pregnant Women

Stool samples were collected with the consent from healthy Koreans who visited the department of endocrinology, Chungnam National University Hospital in order to receive regular checkups. After the collection, each of the stools was put in a 50 mL sterile tube, and immediately placed without a lid of the tube in a pressurized anaerobic jar (3.5 L HP0011A, Oxoid, UK) which was then closed with the lid of the anaerobic jar. A gas mixture of nitrogen:hydrogen:carbon dioxide of 86:7:7 was injected for 20 minutes to replace the air in the anaerobic jar by the gas mixture containing no oxygen. A trace amount of oxygen remaining in the anaerobic jar was reduced into water by reacting with a palladium catalyst and hydrogen in the anaerobic jar, and thus removed. A configuration of such a device is shown in FIG. 1, which was manufactured by the present inventors' laboratory and named as a mobile sample collection bin for absolute anaerobic storage and transportation of clinical samples (FIG. 1).

Example 2: Isolation of Absolute Anaerobic Microorganisms from Stool Samples of Korean Healthy Women The samples collected by the method of Example 1 were transferred to the Korea Research Institute of Bioscience and Biotechnology immediately after the collection, and the anaerobic jar containing the sample was put in an absolute anaerobic chamber (Coy Laboratory Product, USA) filled with a gas mixture (nitrogen:hydrogen:carbon dioxide of 86:7:7). The stool sample diluted with DSM 104 was spread on a DSM 104 agar plate (1.5% w/v) which was previously prepared under absolute anaerobic conditions, and then cultured at 37° C. for 48 hours to select formed colonies. A composition of the DSM 104 medium is as follows.

TABLE 1

| Composition | g/L |
| --- | --- |
| Trypticase peptone | 5 |
| Peptone | 5 |
| Yeast extract | 10 |
| Beef extract | 5 |
| Glucose | 5 |
| $K_2HPO_4$ | 2 |
| Tween 80 | 1 |
| Cysteine-HCl × $H_2O$ | 0.5 |
| Resazurin | 0.001 |
| Salt solution (see Table 2 below) | 40 mL |
| Haemin solution (see below) | 10 mL |
| Vitamin $K_1$ solution (see below) | 0.2 mL |

The vitamin K1, haemin solution and the cysteine are added after the medium has been boiled and cooled under $CO_2$. Adjust pH 7.2 using 8N NaOH. Distribute under $N_2$, and autoclave.

Haemin solution: 50 mg of haemin dissolved in 1 ml of 1 N NaOH

Vitamin $K_1$ solution: 0.1 ml of vitamin $K_1$ dissolved in 20 mL of 95% ethanol

TABLE 2

| Salt solution | |
| --- | --- |
| Composition | g/L |
| $CaCl_2 \cdot 2H_2O$ | 0.25 |
| $MgSO_4 \cdot 7H_2O$ | 0.5 |
| $K_2HPO_4$ | 1 |
| $KH_2PO_4$ | 1 |
| $NaHCO_3$ | 10 |
| NaCl | 2 |

Total 160 colonies were isolated from the stool samples of Korean women by a single colony isolation method, and then molecular biological identification of the isolated strains was performed by colony PCR. The identified strains were confirmed to be total 34 kinds of different species. From 160 strains of the isolated Korean intestinal absolute anaerobic microorganisms, one strain having a high butyrate production ability (>18 mM) was selected and designated as SR79.

The SR79 strain named in the present invention is an absolute anaerobic microorganism isolated by the present inventors directly from the intestine of the healthy Korean, and it was confirmed by molecular biological, physiological/biochemical microbiological identification methods that the strain is a novel microorganism belonging to a novel genus and species different from the standard strain previously reported. The name of the microorganism was suggested as *Agathobaculum butyriciproducens* SR79. The SR79 strain identified in the present invention was accepted as a standard strain for the genus and species of *Agathobaculum butyriciproducens*, which is the new scientific name proposed by the present inventors.

Further, the *Agathobaculum butyriciproducens* SR79 strain was deposited in Korea Research Institute of Bioscience & Biotechnology on Jun. 7, 2016.

Example 3: Investigation of Efficacies of SR79 Strain on Degenerative Brain Diseases and Cognitive and Memory Functions In order to investigate efficacies of the SR79 strain on degenerative brain diseases and cognitive and memory functions, it was intended to examine efficacies of the SR79 strain in Parkinson's disease-induced animal models and Alzheimer's disease mouse animal models.

3-1: Analysis of APPswe and PSEN1-Overexpressed Alzheimer's Disease Mouse Animal Model Experimental Groups Therapeutic effects of the SR79 strain were examined in a mouse animal model (B6C3-Tg(APPswe/PSEN1dE9) 85DboJ, JAX, 004462) which had Alzheimer's disease due to overexpression of Alzheimer's disease-associated APPswe and PSEN1 genes in the brain. This mouse animal model is characterized by noticeable beta-amyloid deposition in the brain from 5 months of age, and Alzheimer's disease-specific cognitive impairment. The mouse animal model was raised with free access to sterile feed and water in a specific pathogen free (SPF) facility maintained at 22° C. to 24° C. under a 12-hr light/dark cycle. The experimental animal groups were divided into a normal mouse group having no overexpression of APP/PSEN1 (Non-Tg) and an Alzheimer's disease mouse group having overexpression of APP/PSEN1, each group divided into a control group treated with 25% glycerol/PBS daily and an experimental group treated with $2.0 \times 10^8$ CFU of the novel microorganism SR79 strain daily. The numbers of the control group and the experimental group in the Alzheimer's disease mouse group having overexpression of APP/PSEN1 were 12 mice per group. In this regard, administration of the mouse groups was begun at 5 months of age, and after administration of the vehicle or the SR79 strain for 9 weeks, a novel object recognition test (NORT) was performed. After administration for 13 weeks, the brains of the mice were removed and immunostained for astrocyte activity in the brain.

3-2: Preparation of LPS (Lipopolysaccharide)-Induced Alzheimer's Disease Experimental Group 8-week-old male C57BL/6J mice were divided into a control group orally administered with 25% glycerol/PBS daily and an experimental group orally administered with $2.0 \times 10^8$ CFU of the novel intestinal microorganism SR79 strain cultured on a DSM 104 solid medium daily for 1 week, and then the SR79 strain-administered group and the control group were intraperitoneally administered with 250 µg/kg of LPS (lipopolysaccharide) daily for 1 week to induce cognitive impairment and Alzheimer's dementia mouse models. In this regard, the group administered with 25% glycerol/PBS as the control group was further divided into a LPS-administered group and a non-LPS-administered group, and used in experiments. 8 mice were assigned to each group. The mice were raised with free access to sterile feed and water in a specific pathogen free (SPF) facility maintained at 22° C. to 24° C. under a 12-hr light/dark cycle.

3-3: Analysis of Cognitive and Memory Functions 3-3-1: Novel Object Recognition Test (NORT)

In order to demonstrate cognitive and memory function-improving effects of the SR79 strain isolated in the present invention on Alzheimer's cognitive impairment, a novel object recognition test (NORT) was performed. In detail, the APP/PSEN1-overexpressing mouse models of Example 3-1 were administered with the control group or the SR79 strain for 9 weeks, and NORT was performed for 2 days. As shown in 3-2, the mouse model of LPS-induced cognitive impairment was administered with LPS for 1 week, and from the next day, NORT was performed for 2 days. On the first day of training, the mouse was placed in a white box of 41.5 cm×20 cm×21.5 cm and allowed to freely explore for 10 minutes. After acclimation for 10 minutes, the mouse was returned to its home cage. At day 2, two identical cylindrical wood blocks were placed at two opposite positions within the box, and then the mouse was allowed to explore the blocks for 10 minutes. After 24 hours, the original cylindrical block (familiar object) and a new rectangular block (new object) were placed in the box, and behaviors of the mouse were observed. At this time, a sniffing time for the mouse to spend touching, sniffing, or moving toward the block was measured. From the overall numbers measured for the two blocks, the time spent in exploring the cylindrical block (familiar object) and the time or number spent in exploring the rectangular block (new object) were measured (FIGS. 2 and 3).

Figure 2A:
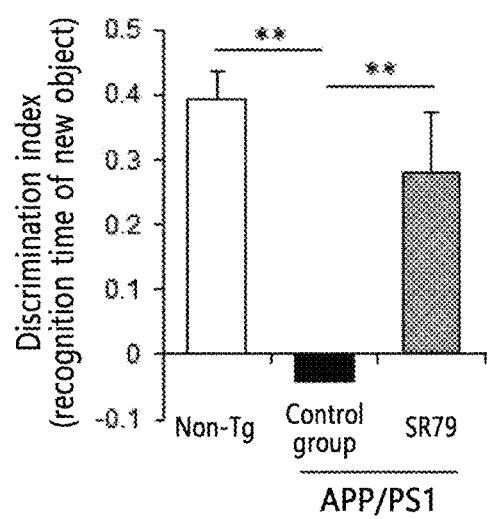
FIGS. 2A and 2B shows a discrimination index indicating effects of improving cognitive and memory functions in a novel object recognition test (NORT, FIG. 2A: recognition time of a new object, FIG. 2B: recognition number of a new object), wherein the test was performed after administering Alzheimer's disease mice (B6C3-Tg(APPswe/PSEN1dE9) 85DboJ, JAX, 004462), in which APP and PSEN1 genes associated with Alzheimer's disease were overexpressed in the brain, with a SR79 strain which is an intestinal microorganism according to the present invention.
Figure 2B:
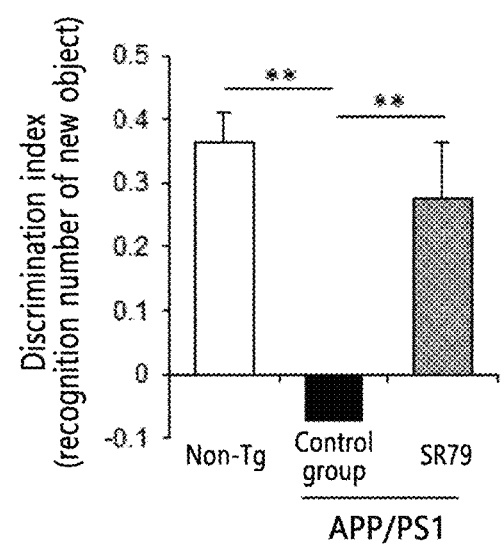

As a result, it was confirmed that the APP/PSEN1-overexpressing Alzheimer's disease mouse showed a remarkable reduction in the exploration time (FIG. 2A) and the exploration number (FIG. 2B) of the new object, as compared with a normal mouse, and administration of the SR79 strain for 9 weeks significantly increased the exploration time and the exploration number of the new object (Students t-test, **p<0.01) (FIG. 2).

The non-LPS-administered group recognized well both the rectangular block which is the new object and the cylindrical block which is the familiar object, whereas non-SR79 strain-treated group of the mouse group administered with LPS for 1 week showed a remarkable reduction in the time spent in exploring the new object due to cognitive impairment, and did not distinguish the familiar object from the new object (Students t-test, p<0.01) (FIG. 3). In contrast, the experimental group which was administered with both LPS and the SR79 strain showed much interest in the new object and clearly distinguished between the familiar object and the new object, as compared with the control group which was administered with only LPS without the SR79 strain (Students t-test,  p<0.01) (FIG. 3). The exploration time was calculated according to (the time spent in exploring the new object−the time spent in exploring the familiar object)/(the time spent in exploring the new object+ the time spent in exploring the familiar object+the time spent in exploring the new object). The above results showed that the SR79 strain had the therapeutic effect on Alzheimer's disease, and the group treated with both LPS and SR79 strain showed improvement in the recognition time of the new object, as compared with the group treated with only LPS, suggesting that the SR79 strain has the effects of improving cognitive and memory functions.

3-3-2. Y-Maze Test

In order to examine the spatial perception- and memory-improving effects of the SR79 strain isolated in the present invention on loss of spatial perception and memory which is caused by Alzheimer's disease, a Y-maze test was performed. In detail, the Y-maze test is a test to examine the spatial perception and short-term memory recovery of experimental animals, and a Y-maze apparatus consists of an enclosed Y-shaped maze which is fabricated using a transparent acrylic sheet (width of 10 cm, length of 40 cm, height of 25 cm) with the arms spaced at an angle of 120 degrees. The test was performed for 10 minutes, and the arms were defined as A, B, and C zones. The experimental animal was placed in one zone and the test was begun to allow the animal to freely explore the maze. In the regard, the frequency and order of entry into each zone were measured to evaluate spontaneous alternation (%). Entry into all three different zones on consecutive choices was scored as 1 point (actual alternation, order of ABC, BCA, CAB, etc.), and if not entered consecutively, the score was not recognized. The spontaneous alternation (%) was calculated according to the total number of alternations/(the total number of entries−2)×100.

The results of the Y-maze test showed that the mice of the experimental group administered with both LPS and SR79 strain showed a statistically significant increase in spontaneous alternation, as compared with the mice administered with only LPS (Student's t-test, *p<0.05) (FIG. 4). These results confirmed that SR79 strain has the effects of improving a decline in the spatial perception and short-term memory which is caused by Alzheimer's disease, indicating an effect of memory improvement.

3-4. Analysis of Neuroinflammation Marker

Figure 5A:
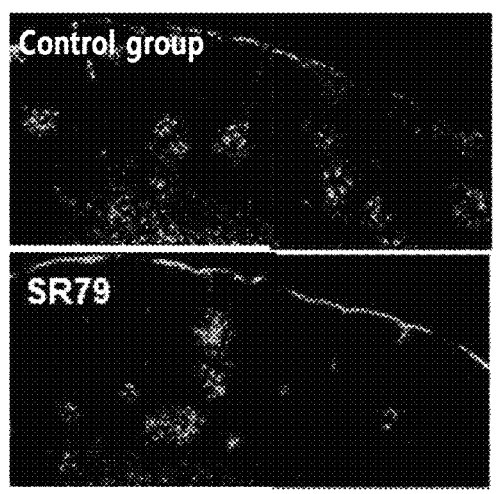
FIG. 5A is a photograph and FIG. 5B is a graph showing the results of immunostaining of astrocytes activated in the brain after administering Alzheimer's disease mice (B6C3-Tg(APPswe/PSEN1dE9)85DboJ, JAX, 004462), in which APP and PSEN1 genes associated with Alzheimer's disease were overexpressed in the brain, with a SR79 strain which is the intestinal microorganism according to the present invention.
Figure 5B:
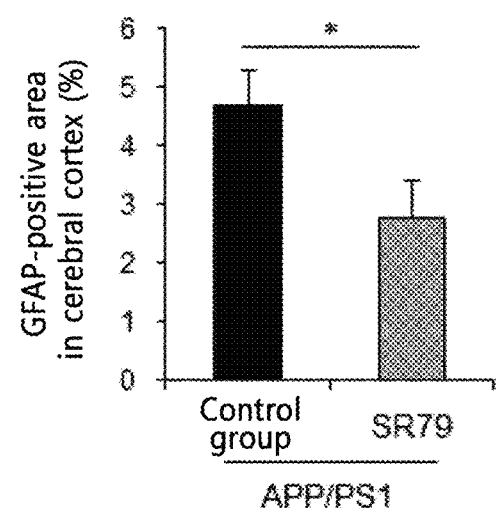

In order to examine the effect of SR79 on neuroinflammation in Alzheimer's disease mice overexpressing APP/PSEN1, immunostaining of cerebral cortex was performed using an astrocyte-specific GFAP (Glial fibrillary acidic protein) antibody, and the levels of astrocytes activated in the cerebral cortex of the control and experimental group mice were measured and compared (FIG. 5). FIG. 5A is a photograph showing the result of immunostaining astrocytes activated in the brain of the Alzheimer's disease mouse animal model by administration of the SR79 strain, and FIG. 5B is a graph showing the result of comparing the immunostaining levels of the astrocytes activated in the brains of the Alzheimer's disease mouse animal models administered with the vehicle (control group) and the SR79 strain (SR). As shown in FIG. 5, the levels of the astrocytes activated in the cerebral cortex were significantly reduced by administration of the SR79 strain (Student's t-test, *p<0.05).

Further, in order to examine the inhibitory effect of SR79 on neuroinflammation in LPS-treated mouse models, Western blotting was performed in the cerebral cortex of LPS-administered mouse models using an Iba-1 (ionized calcium-binding adapter molecule 1) antibody which is a marker for the activity of microglial cells mediating neuroinflammation (FIG. 6).

The experimental results showed that expression of Iba-1 which is a marker for activated microglial cells in the cerebral cortex was increased by LPS administration, and the LPS and SR79 strain-administered group showed a significant reduction in Iba-1 expression (Student's t-test, *p<0.05) (FIG. 6). Based on the results, the inhibitory effects of the SR79 strain on neuroinflammation were also confirmed at the individual level.

3-5. Analysis of APP (Amyloid Precursor Protein) Phosphorylation

In order to examine the inhibitory effects of SR79 on the risk factors for Alzheimer's disease, proteins of the cerebral cortex of the LPS-administered mouse model were isolated and phosphorylation of APP (Amyloid precursor protein) was analyzed by Western blotting using a pAPP antibody.

The experimental results showed that pAPP expression in cerebral cortex was remarkably increased by LPS administration. In contrast, p-APP was not increased in the LPS and SR79 strain-administered group (Student's t-test, NS; not significant), indicating low risk of Alzheimer's disease (FIG. 7). Based on the results, the SR79 strain was confirmed to have the effect of preventing Alzheimer's disease.

3-6. Preparation of 6-OHDA (6-Hydroxyldopamine)-Induced Parkinson's Disease Experimental Group 9-week-old male C57BL/6J mice were used as experimental animals. The mice were raised with free access to sterile feed and water in a specific pathogen free (SPF) facility maintained at 22° C. to 24° C. under a 12-hr light/dark cycle. In the experimental animal groups, a control group was orally administered with 25% glycerol/PBS daily and an experimental group was orally administered with $2.0\times10^8$ CFU of the novel intestinal microorganism SR79 strain daily for 1 week, and then 6-OHDA (6-hydroxyldopamine) was injected into the brains of the mice to induce dopaminergic neuronal cell death. The number of mice assigned to the control group and the experimental group was 5 and 6 mice, respectively. Each of the mice was anesthetized with a mixture of ketamine and rumpun to perform the experiment. 6-OHDA was directly injected into the brain to produce 70% to 80% of dopaminergic cell loss in the substantia nigra of the brain, which corresponds to the progression of early Parkinson's disease. To prevent destruction of noradrenergic neurons, 25 mg/kg of desipramine was intraperitoneally administered at 30 minutes before 6-OHDA injection, and a total of 6 μg of 6-OHDA was injected into the left striatum (coordinates of the microinjection: anterior-posterior=+1.3, medio-lateral=−1.8, dorso-ventral=−3.6). As described above, after direct injection of 6-OHDA into the brain, the surgical site was sutured and disinfected, and then the body temperature of the mice was maintained at 37° C. warmer.

Parkinson's disease was induced through the above surgical treatment, and then the control group and the experimental group were administered with 25% glycerol/PBS and $2.0\times10^8$ CFU of SR79 strain daily, respectively, before a behavioral test such as a d-amphetamine-induced rotation test.

3-7. Behavioral Test of Parkinson's Disease-Induced Animal Model

It is known that as the dopaminergic cell death by 6-OHDA is increased, a lesion on one side of the brain becomes severe, and thus the number of behavioral rotations in the experimental animal is increased. In order to evaluate severity of movement abnormalities by dopaminergic cell death, the mouse was intraperitoneally administered with 5 mg/kg of dextroamphetamine (d-amphetamine) at 6 days after 6-OHDA injection, and asymmetric rotational behaviors were observed. In detail, after administration of dextroamphetamine, the mouse was placed in a cylinder with a diameter of 20 cm, and the number of counter-clockwise rotations was measured for 30 minutes to evaluate rotational behaviors. The experimental results showed that a statistically significant reduction in the rotational behaviors was observed in the experimental group that ingested the SR79 strain, as compared with the control group that ingested 25% glycerol/PBS (FIGS. 8 and 9). These results suggest that the SR79 strain has the effects of preventing and treating movement disorders in Parkinson's disease.

Effect of the Invention

Since the intestinal microorganism *Agathobaculum butyriciproducens* SR79 strain of the present invention may have effects of inhibiting neuroinflammation and effects of improving movement regulation and cognitive and memory functions in animal models with degenerative brain diseases such as Parkinson's disease and Alzheimer's disease, the strain may be usefully applied to foods, medicines, or feeds for preventing or treating brain diseases including Alzheimer's disease, Parkinson's disease, mild cognitive impairment, etc., and therefore, it is very useful in the related industries.

What is claimed is:

1. A pharmaceutical composition for preventing or treating degenerative brain diseases, the composition comprising: (a) one or more components selected from the group consisting of a strain of *Agathobaculum butyriciproducens*, a vesicle derived from the strain, a culture of the strain, and a concentrate of the culture as an active ingredient, and (b) an enteric coating.

2. The pharmaceutical composition according to claim 1, wherein the degenerative brain disease is Alzheimer's disease, Parkinson's disease, mild cognitive impairment, meningitis, stroke, dementia, Huntington's disease, or Creutzfeldt-Jakob disease.

3. The pharmaceutical composition according to claim 1, wherein the composition has inhibitory effects on movement disorders which are caused by dopaminergic neuronal cell death.

4. The pharmaceutical composition according to claim 1, wherein the composition has inhibitory effects on neuroinflammation.

5. The pharmaceutical composition according to claim 1, wherein the composition has effects of improving cognitive and memory functions.

6. A health functional food composition for preventing or improving degenerative brain diseases, the composition comprising: (a) one or more components selected from the group consisting of a strain of *Agathobaculum butyriciproducens*, a vesicle derived from the strain, a culture of the strain, and a concentrate of the culture as an active ingredient; and (b) an enteric coating.

7. A feed composition for preventing or improving degenerative brain diseases, the composition comprising: (a) one or more components selected from the group consisting of a strain of *Agathobaculum butyriciproducens*, a vesicle derived from the strain, a culture of the strain, and a concentrate of the culture as an active ingredient and (b) an enteric coating.

8. The pharmaceutical composition according to claim 1, wherein the *Agathobaculum butyriciproducens* is *Agathobaculum butyriciproducens* SR79 strain with Accession No. KCTC13036BP.

* * * * *